United States Patent [19]

Siri

[11] Plant 5,181

[45] Jan. 24, 1984

[54] MINIATURE CARNATION

[75] Inventor: Angelo J. Siri, San Francisco, Calif.

[73] Assignee: Siri Brothers Nursery, Inc., East Palo Alto, Calif.

[21] Appl. No.: 397,555

[22] Filed: Jul. 12, 1982

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Limbach, Limbach & Sutton

[57] ABSTRACT

A miniature carnation having blossoms which are variegated pink and white.

2 Drawing Figures

BACKGROUND OF THE NEW PLANT

This invention comprises a new and distinct miniature carnation variety that has its own set of characteristics that set it apart from all other varieties of miniature carnations. The newly discovered variety, called "Jenny," originated as a sport of Apache of a patented variety, U.S. Plant Pat. No. 4,100.

The botanical classification of the new variety is Dianthus Caryophyllus Longicaulis. The commercial classification is Miniature Carnation. The plant takes the form of a bush.

Asexual propagation of the newly discovered miniature carnation variety has been made at Siri Brothers Nursery, Inc. at East Palo Alto, Calif. by taking cuttings. The cuttings so taken and grown, have consistently produced flowers that have the new and distinct characteristics hereinafter described.

DESCRIPTION OF THE DRAWINGS

This new variety of miniature carnation plant is illustrated by the accompanying drawings which show the color characteristics of the flower as nearly true as it is reasonably possible to obtain through conventional photographic procedures.

DESCRIPTION OF THE NEW PLANT

Figure 1:
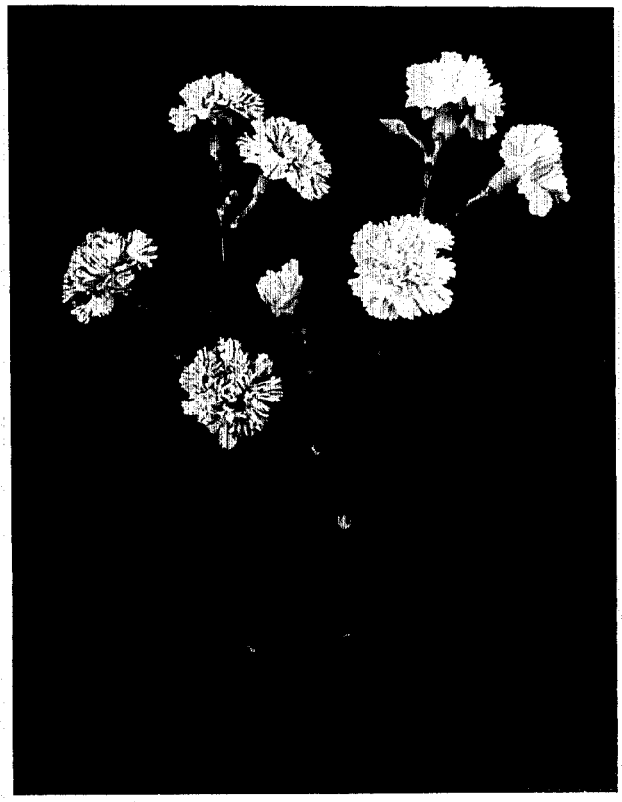
FIG. 1. PRIOR ART
FIG. 1 shows sprays and stems of the new variety Jenny on the right and the prior Apache on the left.
Figure 2:
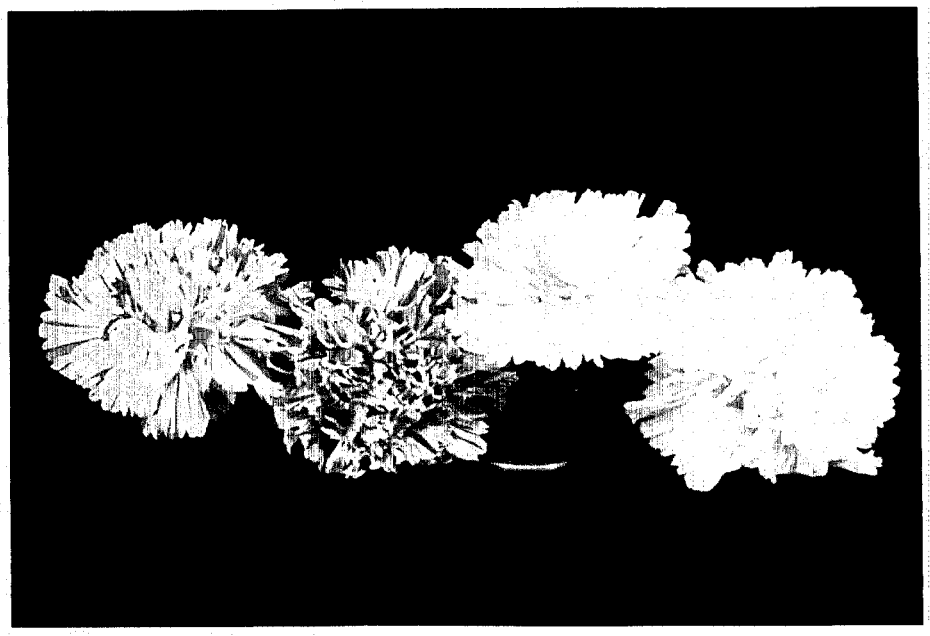
FIG. 2 shows the blooms of the new variety Jenny on the right and the prior Apache on the left.

The following detailed description of the new variety is based on my detailed observations of the new cultivar which were made at Siri Brothers Nursery Inc. at 940 O'Connor Street, East Palo Alto, Calif. The response time, blooming period, total vigor, and color may vary slightly with varying environmental conditions such as temperature, length of day, and light intensity. The color description is given by designation "H" for hue and "L" for lightness in color chart references designated "LCC" for Limit Color Cascade, Munsell Color, Baltimore, Md. and "RHS" for The Royal Horticultural Colour Chart, Royal Horticultural Society, London, England.

Flower

Description of the color of the bloom: the bloom appears to be pink and white variegated. The white is RHS White Group 155D but brighter, both top side and underside of the petals. The pink is LCC H-40 L-5 topside of petal and LCC H-40 L-3 bottomside of the petals. Upon close examination of the bloom we find some purple specks, blotches and stripes. The purple is LCC H-45 L-12 topside and bottomside of petal and LCC H-45 L-9 bottomside of petals. There are also some other shades of purple on some of the petals although these are few and small. The bloom gives the appearance of pink and white variegated though there are some purple markings in it.

Petalage

Petal color:

*Topside base of petal.*—White RHS White Group 155D but brighter, Pink LCC H-40 L-5, Purple LCC H-45 L-12.

*Topside middle of petal.*—White RHS White Group 155D but brighter, Pink LCC H-40 L-5, Purple LCC H-45 L-12.

*Topside outside of petal.*—White RHS White Group 155D but brighter, Pink LCC H-40 L-5, Purple LCC H-45 L-12.

*Underside base of petal.*—White RHS White Group 155D but brighter, Pink LCC H-40 L-3, Purple LCC H-45 L-12 and LCC H-45 L-9.

*Underside middle of petal.*—White RHS White Group 155D but brighter, Pink LCC H-40 L-3, Purple LCC H-45 L-12 and LCC H-45 L-9.

*Underside outside of petal.*—White RHS White Group 155D but brighter, Pink LCC H-40 L-3, Purple LCC H-45 L-12 and LCC H-45 L-9.

Distinguishing Characteristics Between the New Variety and Parent

The only distinguishing characteristic is the color of the bloom. The parent is purple and white variegated and the sport is pink and white variegated.

Similar Characteristics of the New Variety and Parent

All other characteristics except the color are the same.

I claim:

1. A new and distinct variety of miniature carnation plant, substantially as herein shown and described.

* * * * *

PRIOR ART